United States Patent [19]
Billington

[11] 3,974,271
[45] Aug. 10, 1976

[54] LIPSTICK CONTAINING 8-AMINO-2-(AZO-BENZENE-4-SULPHONIC ACID)-1-NAPHTHOL-3,6-DISULPHONIC ACID OR AN EDIBLE SALT THEREOF

[75] Inventor: Arthur Ernest Billington, Watford, England

[73] Assignee: Beecham Group Limited, England

[22] Filed: Feb. 3, 1975

[21] Appl. No.: 546,272

Related U.S. Application Data

[62] Division of Ser. No. 387,749, Aug. 13, 1973, Pat. No. 3,892,872.

[30] Foreign Application Priority Data
Aug. 19, 1972  United Kingdom............... 38761/72
Oct. 5, 1972  United Kingdom............... 45922/72

[52] U.S. Cl. ................................................. 424/64

[51] Int. Cl.² ........................................ A61K 7/025
[58] Field of Search ..................................... 424/64

[56] References Cited
UNITED STATES PATENTS
3,800,034  3/1974  Kircher et al.................... 424/64 X FOREIGN PATENTS OR APPLICATIONS
858,183  1/1961  United Kingdom................ 260/198

OTHER PUBLICATIONS
Chem. Abstr., 58, 1450c (1963).

*Primary Examiner*—Frederick E. Waddell

[57] ABSTRACT

A lipstick composition comprising 8-amino-2-(azo-benzene-4-sulphonic acid) 1-naphthol-3 6-disulphonic acid as a coloring material, named "Red AB".

4 Claims, No Drawings

LIPSTICK CONTAINING 8-AMINO-2-(AZO-BENZENE-4-SULPHONIC ACID)-1-NAPHTHOL-3,6-DISULPHONIC ACID OR AN EDIBLE SALT THEREOF

This is a division of application Ser. No. 387,749, filed Aug. 13, 1973, now U.S. Pat. No. 3,892,872, dated July 1, 1975.

This invention relates to edible colouring materials in particular for use in beverage and cosmetic compositions.

A compound suitable for inclusion into beverages as a colouring agent must have three requirements: it must have a good tinctorial power; it must be biologically acceptable; and it must be stable in the presence of fruit acids and strong reducing agents such as sulphurous and ascorbic acids which are commonly present in such compositions. One red dye which is commonly used for colouring beverages is colour index constitution No 17200 (CI. Food Red 12) commonly known as "Red 10B" which is the disodium salt of 8-amino-2-(phenylazo)-1-naphthol-3 6-disulphonic acid of formula (I)

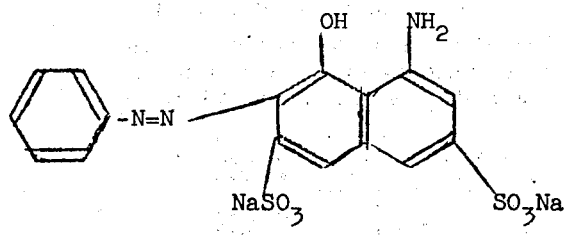

However one undesirable feature of Red 10B is that it is now known to produce an increase in the level of Heinz bodies in the bloostream when administered in high concentrations in the diet of test animals. These are bodies which appear in ageing red cells of blood. As a result Red 10B is no longer suitable for universal unrestricted use in food. A red colouring material which has been shown not be produce Heinz bodies is disclosed in British Patent No. 1,270,656 and is 8-acetamido-2-(azobenzene-4-sulphonic acid)-1-naphthol-3 6-disulphonic acid of formula (II):

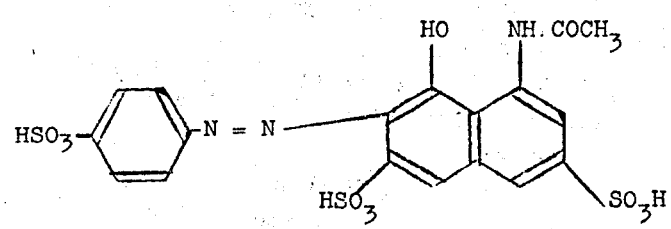

Although the above patent discloses the use of compound II in a variety of foodstuffs, it is particularly concerned with the colouring of sausage meats. Whilst it is stable in sausage meat compositions we have found, however that the compound (II) is undesirable for use in beverages such as fruit cordials or carbonated drinks because the acetamide group is relatively unstable in the acid conditions (pH 3.0–3.5) found in such products; the compound is hydrolysed to the compound of formula (III):

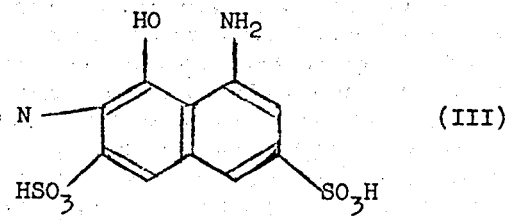

which is 8-amino-2-(azo-benzene-4-sulphonic acid)-1-naphthol-3 6-disulphonic acid.

Compound (III) has previously been used as a chemical reagent [see R. Oda and R. Baba, Kogyo Kagaku Zasshi 65 294 (1962); Chemical Abstracts 58 1450C (1963)] and similar compounds are disclosed in British Patent No. 858,183 as dyestuffs for dyeing textile materials. However compound (III) has not been incorporated as a colouring material in foodstuffs or cosmetics. It has now been found that compound (III) is in its own right useful as a colouring agent for foodstuffs or compositions intended for contact with the mouth, for example lipstick composition. It has a higher tinctorial power than Red 10B and can therefore be used at lower concentrations (by weight) to produce the same effect thus resulting in greater safety in use as a food additive. Furthermore this compound is stable in acid conditions and does not produce Heinz bodies in the blood.

The present invention therefore provides an edible composition comprising 8-amino-2-(azo-benzene-4-sulphonic acid)-1-naphthol-3 6-disulphonic acid or an edible salt thereof together with an edible diluent or carrier. We have named the compound of formula III "Red AB" and it will be referred to as such throughout this specification.

From a second aspect the present invention provides an edible composition comprising an edible diluent or carrier in which 8-amino-2-(azo-benzene-4-sulphonic acid)-1-naphthol-3 6-disulphonic acid or an edible salt thereof is incorporated as such.

By the term "incorporated as such" herein we mean that the compound itself is incorporated into the composition and not a precursor or derivative of the compound, which may be transformed to Red AB in situ.

Red AB and/or its salts may be used to colour all types of edible materials which are intended for consumption or contact with the mouth. Suitable diluents and carriers which may be coloured include, for example, beverages such as soft drinks; fruit ades; wines; beverage concentrates such as syrups powder concentrates or tablets; dietary type foods: ice creams sherberts and ices; ice milk products; bakery products; icing; confections such as boiled sweets and confection toppings syrups, jams and flavours fruit gelatin desserts, cake mixes; meat products; cough syrups and other medicinal preparations intended for oral administration; dental preparations such as pastes powders foams; mouth washes and similar oral antiseptic liquids and cosmetic formulations in particular lipsticks.

Red AB and its salts are particularly advantageous for use in colouring carbonated and non-carbonated soft drinks and syrup concentrates which may be made up to such drinks. In particular we have found that Red AB produces an intense bluish red hue which is particularly suitable for producing the colours customarily associated with dark-coloured fruits such as blackcurrant, black cherry blackberry, blueberry etc.

Another composition in which the amount of organic colouring material is significant is a lipstick composition. We have found that Red AB is also useful for incorporating into lipstick compositions.

Accordingly the invention further provides a lipstick composition comprising 8-amino-2-(azo-benzene-4-sulphonic acid)-1-naphthol-3 6-disulphonic acid or an edible salt thereof together with a suitable carrier.

The salts which may be included in the compositions of this invention may be the mono-, di-, and/or tri-salts of Red AB. Suitable salts for inclusion into beverages include alkali-metal salts of Red AB, preferably the sodium salts. For lipstick compositions the compound is preferably converted to an insoluble salt for example a barium or calcium salt.

Red AB or its salts are incorporated in the material to be coloured in an amount required to attain the desired level of colouring. Preferred amounts of Red AB for use in syrups cordials ets, are 75 to 300 mg/kg; and in ready to drink beverages from 1–75 mg/kg, preferably 25–50 mg/kg.

Preferred amounts for use in lipstick compositions are from 1–10% by weight.

The invention is illustrated by the following examples:

EXAMPLE 1

Preparation of 8-amino-2-(azo-benzene-4-sulphonic acid)-1-naphthol-3 6-disulphonic acid Sulphanilic acid (14.4g; 0.0833 mole) and sodium carbonate (4.42g; 0.0416 mole) were dissolved in water (330ml), cooled to 0° then added with stirring, to sodium nitrite (5.25g; 0.076 mole) in water (76ml) at 0°. This mixture was added with stirring to 5N Hydrochloric acid (32 ml) at 0° then the resultant suspension was added rapidly to a solution of 8-amino-1-naphthol-3 6-disulphonic acid, monosodium salt (30g; 0.0839 mole) and sodium hydroxide (10 g; 0.25 mole) in water (125 ml) at 0°. The violet solution was stirred for 30 minutes then 5N Hydrochloric acid was added dropwise until pH 7.0 was achieved. The water was removed on a rotary evaporator then the resultant brittle solid was warmed on a water bath with ethanol (750ml) and water (200ml) with occasional shaking for 2 hours. The deep violet solution was decanted then left in a refrigerator overnight whereupon the dye precipitated. This was filtered off then dried at 68° in a vacuum oven. Yield =30.15g (76.9% based on sulphanilic acid).

EXAMPLE 2

A blackcurrant syrup was prepared having the following composition:

| | |
|---|---|
| Blackcurrant juice | 40% (v/v) |
| Sugar | 60% (v/v) |
| Sulphur dioxide (preservative) | 300 mg/kg |
| Colouring:   Red AB | 125 mg/kg |
| Tartrazine | 23 mg/kg |
| Green S | 2.7 mg/kg |

EXAMPLE 3

Comparison with Red 10B

The quantities of colouring agents required to produce the same colouring effect for a blackcurrant syrup using (i) Red 10B and (ii) Red AB are shown below:

| (i) Composition using Red 10B | | (ii) Composition using Red AB | |
|---|---|---|---|
| Red 10B | 133mg/kg | Red AB | 125 mg/kg |
| Tartrazine | 23mg/kg | Tartrazine | 23mg/kg |
| Green S | 2.7 mg/kg | Green S | 2.7 mg/kg |
| Total Colour | 158.7mg/kg | Total Colour | 150.7 mg/kg |

Thus a lower concentration of Red AB is sufficient to produce the same intensity of colour as Red 10B.

EXAMPLE 4

A lipstick composition was prepared as follows:

| | | |
|---|---|---|
| Base | Castor Oil | 69.50 |
| | Cocoa Butter substitute | 14.00 |
| | Candelilla Wax | 9.00 |
| | Beeswax | 6.00 |
| | Carnauba Wax | 1.50 |
| | | 100.00 |
| Base | | 95% |
| 8-amino-2-(azo-benzene-4-sulphonic acid)-1-naphthol-3,6-disulphonic acid | | 5% |

I claim:

1. A lipstick comprising an amount of 8-amino-2-(azo-benzene-4-sulphonic acid)-1-naphthol-3,6-disulphonic acid or an edible salt thereof sufficient to impart the desired degree of red color to the lipstick in combination with a carrier suitable for formation of a lipstick.

2. A lipstick according to claim 1 wherein the 8-amino-2-(azo-benzene-4-sulphonic acid)-1-naphthol-3,6-disulphonic acid is in the form of an insoluble edible salt.

3. A lipstick according to claim 2 wherein the salt is the barium or calcium salt.

4. A lipstick according to claim 1 wherein the amount of 8-amino-2-(azo-benzene-4-sulphonic acid)-1-naphthol-3,6-disulphonic acid or edible salt thereof is 1–10% by weight.

* * * * *